United States Patent
Lee et al.

(10) Patent No.: US 9,232,297 B2
(45) Date of Patent: Jan. 5, 2016

(54) DEVICE FOR SUPPLEMENTING VOICE INCLUDING SENSING UNIT AND METHOD FOR CONTROLLING THE SAME

(71) Applicant: INHA-INDUSTRY PARTNERSHIP INSTITUTE, Incheon (KR)

(72) Inventors: Woo-Key Lee, Incheon (KR); Young-Mo Kim, Seoul (KR); Jaehwan Kim, Incheon (KR); Jeong-Seok Choi, Seoul (KR); Jae-Yol Lim, Incheon (KR); Soon-Hyoung Park, Seoul (KR); Jong-Su Song, Incheon (KR)

(73) Assignee: Inha-Industry Partnership Institute, Incheon (KR)

( * ) Notice: Subject to any disclaimer, the term of this patent is extended or adjusted under 35 U.S.C. 154(b) by 121 days.

(21) Appl. No.: 13/739,926

(22) Filed: Jan. 11, 2013

(65) Prior Publication Data
US 2013/0182873 A1    Jul. 18, 2013

(30) Foreign Application Priority Data

Jan. 12, 2012  (KR) .................. 10-2012-0003868
Mar. 6, 2012  (KR) .................. 10-2012-0022979
Apr. 17, 2012  (KR) .................. 10-2012-0039843

(51) Int. Cl.
*A61F 2/20* (2006.01)
*H04R 1/14* (2006.01)
*G10L 13/04* (2013.01)

(52) U.S. Cl.
CPC .. *H04R 1/14* (2013.01); *A61F 2/20* (2013.01); *G10L 13/043* (2013.01); *A61F 2002/206* (2013.01)

(58) Field of Classification Search
CPC ............... A61F 2002/206; A61F 2/20; G10L 2021/0575
See application file for complete search history.

(56) References Cited

U.S. PATENT DOCUMENTS

| | | | |
|---|---|---|---|
| 5,888,187 A | * | 3/1999 | Jaeger et al. .................... 600/23 |
| 2007/0127748 A1 | * | 6/2007 | Carlile et al. ................ 381/312 |
| 2014/0079233 A1 | * | 3/2014 | Kamradt et al. ............... 381/70 |
| 2014/0277272 A1 | * | 9/2014 | Lindenthaler .................. 607/48 |
| 2014/0358551 A1 | * | 12/2014 | Liu et al. ..................... 704/271 |

FOREIGN PATENT DOCUMENTS

| | | |
|---|---|---|
| JP | 61-31150 A | 2/1986 |
| JP | 11-69476 | 3/1999 |
| JP | 2000-188794 A | 7/2000 |
| JP | 2005-150884 | 6/2005 |
| JP | 2008-544832 A | 12/2008 |

(Continued)

OTHER PUBLICATIONS

Japanese Office Action issued Dec. 26, 2013 in counterpart Japanese Patent Application No. 2013-004102. (3 pages in Japanese).

(Continued)

*Primary Examiner* — Matthew Eason
(74) *Attorney, Agent, or Firm* — NSIP Law

(57) ABSTRACT

A device for supplementing a voice includes: a sensing unit sensing a bio-signal corresponding to a first vibration of vocalization and generating a first signal corresponding to the bio-signal; a vibration unit generating a second vibration using the first signal; and a power unit supplying a power to the sensing unit and the vibration unit.

23 Claims, 5 Drawing Sheets

(56) References Cited

FOREIGN PATENT DOCUMENTS

| KR | 20-0288738 | 9/2002 |
| KR | 20-0322843 | 8/2003 |
| KR | 20-0342565 | 2/2004 |
| KR | 20-0399231 | 10/2005 |
| KR | 10-2009-0131364 | 10/2009 |

OTHER PUBLICATIONS

Korean Office Action issued on Apr. 10, 2013 in counterpart Korean Patent Application No. 10-2012-0022979. (3 pages in Korean).

Korean Office Action issued on May 10, 2013 in counterpart Korean Patent Application No. 10-2012-0003868. (5 pages in Korean).

\* cited by examiner

DEVICE FOR SUPPLEMENTING VOICE INCLUDING SENSING UNIT AND METHOD FOR CONTROLLING THE SAME

This application claims the benefit of Korean Patent Application No. 10-2012-0003868, filed on Jan. 12, 2012, No. 10-2012-0022979, filed on Mar. 6, 2012 and No. 10-2012-0039843, filed on Apr. 17, 2012, which are hereby incorporated by reference in their entirety.

BACKGROUND

1. Field of the Disclosure

The present disclosure relates to a device for supplementing a voice, and more particularly, to a device for supplementing a voice that generates a vibration for sound by attachment to or contact with a body and a method for controlling the device.

2. Discussion of the Related Art

A sound of human beings is expressed through a voice. The voice generated by vocal organs is classified into: a pronunciation or a speech sound for communication of linguistic transinformation; and a non-linguistic vocalization irrelevant to communication. While a sound of animals without a vowel is differently felt by a listener according to his own thought, a voice of human beings with a vowel constitutes various discriminable sounds. As a result, human beings communicate with one another by the voice.

The voice of human beings is an essential element for communication, and various vocal organs of a nervous system and a respiratory system relate to generation of the voice. Among the nervous system, a central nervous system and a peripheral nervous system relate to generation of the voice. A cranium or a nucleus of a brain cell which is necessary for generation of language is disposed in a brain stem of the central nervous system. A cerebellum of the central nervous system has a function of tuning a control of muscle for operation, and a cerebral hemisphere of the central nervous system performs a dominant role in language function. There are the fifth brain nerve relating to movement of a chin, the seventh brain nerve relating to movement of lips, the tenth brain nerve relating to movement of a pharynx and a larynx, the eleventh brain nerve relating to movement of a pharynx and the twelfth brain nerve relating to movement of a tongue in a cranial nerve relating to generation of the speech sound. A nersus laryngeus superior and a recurrent laryngeal nerve of the peripheral nervous system which are separated from a vagus nerve directly relate to movement of the larynx.

The speech sound is generated by an intimate interaction among a lower respiratory system, a larynx and a vocal track. Specifically, the larynx in a neck of human beings which relates to a voice is disposed between second and third cervical vertebrae (C2, C3) when one is a baby and moves to be disposed between third and sixth cervical vertebrae (C3, C6) when one is an adult. The larynx has functions of swallowing, cough, occlusion, respiration and vocalization. Specifically, the larynx includes a vocal cord as a source of a voice. The vocal cord has a wrinkled double-layered shape crossing an inner space of the larynx. A flow of an expired air vibrates the vocal cord and a control of the expired air efficiently supplies a sound energy during vocalization. When the vocal cord is properly strained and closed, the expired air vibrates the vocal cord, and a glottis that is a gap between the vocal cord and an arytenoid of the larynx opens and closes with a specific period to cut and connect the expired air. The discontinuous flow of the expired air functions as the source of the voice. When the air expired to exterior by respiration passes though the glottis, the air vibrates the vocal cord. Although the sound generated in the larynx is a consonant, a vowel is generated by means of a palate, a tongue, teeth and lips.

A voice disability may be defined as a problem such that a pitch, a loudness, a quality and a flexibility of a voice are not proper to a gender, a physique, a social environment and a geographical position. The innate or acquired voice disability may be cured by a surgery of expanding or reducing the vocal cord of the larynx. However, the voice disability is not completely cured and an effect of the surgery is not accurate. Various methods for determining the voice disability, for example an investigation of voice symptom, an investigation of voice usage pattern, an acoustic test and aerodynamic test, have been developed, and whether the voice disability exists or not is determined by the various methods to a certain extent.

The voice disability having various types is classified into a functional voice disability and an organic voice disability. Most of voice disabilities may result from a disability of the vocal cord, and the disability of the vocal cord may be caused by generation of a tumefaction, a tearing or an abnormal substance due to an external environmental factors.

For the purpose of overcoming the voice disability, an artificial vocal cord has been suggested. In a method of using the artificial vocal cord, an artificial connecting tube is inserted between a respiratory tract and an esophagus so that the air of the respiratory tract can be induced to the esophagus and can vibrate an esophageal sphincter instead of the vocal cord. When the esophageal sphincter vibrates, a flow of the air remaining in the respiratory tract is cut so that vocalization can be performed. However, the voice by the artificial vocal cord has a poor quality to have a mere conversation. Accordingly, a number of troubles in a social life are still not surmounted.

Besides the vocal disability, people suffer from a vocal disorder such that vocalization is not controlled due to an uncontrollable voice. For example, a voice may be too loud, too quiet or too hoarse. Although the surgery of the larynx or the vocal cord is performed to overcome the vocal disability or the vocal disorder, the curing method is not a perfect solution because the surgery is sometimes impossible.

SUMMARY

Accordingly, the present disclosure is directed to a device for supplementing a voice and a method for controlling the device that substantially obviate one or more of the problems due to limitations and disadvantages of the related art.

An advantage of the present disclosure is to provide a device for supplementing a voice where vocalization of excellent quality is obtained by generating a vibration at or near a vocal cord.

Another advantage of the present disclosure is to provide a device for supplementing a voice where vocalization of excellent quality is obtained by generating an amplified vibration or an attenuated vibration from an original vibration.

Another advantage of the present disclosure is to provide a device for supplementing a voice where vocalization of excellent quality is obtained by generating a frequency modulated vibration for an original vibration.

Additional features and advantages of the invention will be set forth in the description which follows, and in part will be apparent from the description, or may be learned by practice of the invention. These and other advantages of the invention will be realized and attained by the structure particularly pointed out in the written description and claims hereof as well as the appended drawings.

To achieve these and other advantages and in accordance with the purpose of the present invention, as embodied and broadly described, a device for supplementing a voice includes: a sensing unit sensing a bio-signal corresponding to a first vibration of vocalization and generating a first signal corresponding to the bio-signal; a vibration unit generating a second vibration using the first signal; and a power unit supplying a power to the sensing unit and the vibration unit.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, examples of which are illustrated in the accompanying drawings. Wherever possible, similar reference numbers will be used to refer to the same or similar parts.

A glottis between vocal cords of a larynx is periodically opened and closed and a discontinuous flow of an expired air vibrates the vocal cords to generate a voice. A loudness of the voice corresponds to an amount of the discontinuous flow of the expired air and a pitch of the voice corresponds to a frequency of the vibration. A number of the vibration of the vocal cords per second is defined as an individual fundamental frequency. Since a force of a muscle narrowing the vocal cords, a thickness of the vocal cords and a size and a shape of the glottis are different according to individuals, the flow of an expired air through the vocal cords is also different according to individuals. For example, since women or children have a narrow glottis, the flow of an expired air is fast and the vibration has a relatively high frequency. As a result, women or children have a relatively high frequency and a relatively high pitch as compared with men.

Although human beings have various voices due to the vibration of the vocal cords, one may have an innate or acquired voice disability such that the vocal cords never vibrate or do not vibrate appropriately. The device according to the present disclosure may provide a fundamental vibration, an amplified vibration, an attenuated vibration or a frequency modulated vibration for the voice.

In illustration, an original vibration by a vocal cord may be referred to as a first vibration and an electric signal corresponding to the first vibration may be referred to as a first signal. In addition, a vibration which is obtained using the original vibration may be referred to as a second vibration and an electric signal corresponding to the second vibration may be referred to as a second signal.

Figure 1:
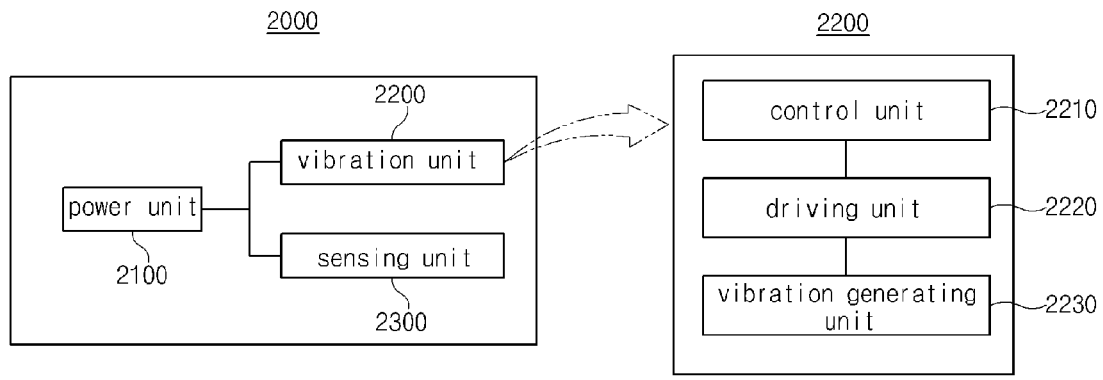
FIG. 1 is a block diagram showing a device for supplementing a voice according to an embodiment of the present invention.

FIG. 1 is a block diagram showing a device for supplementing a voice according to an embodiment of the present invention.

In FIG. 1, a device 2000 for supplementing a voice includes a power unit 2100, a vibration unit 1200 and a sensing unit 2300. The power unit 2100 supplies a power to the vibration unit 2200 and the sensing unit 2300. For example, the power unit 2100 may include a rechargeable battery. In addition, the battery may be formed of a material having biocompatibility based on the point that the device 2000 may be installed in a body such as a vocal cord.

The sensing unit 2300 senses a bio-signal corresponding to a first vibration for vocalization. In addition, the sensing unit 2300 generates a first signal corresponding to the bio-signal and sends the first signal to the vibration unit 2200. The first signal may have a sinusoidal wave. The sensing unit 2300 may include a biometric sensor that senses a bio-signal such as a pulse signal of a nerve relating to the first vibration for vocalization adjacent to the vocal cord, an electromyographic signal according to muscle contraction, a sound signal according to sound or vibration caused by the first vibration for vocalization and a brain signal and may generate the first signal corresponding to the bio-signal. For example, the biometric sensor may include a mike-sensor sensing sound or vibration relating to the first vibration for vocalization adjacent to the vocal cord.

Further, the biometric sensor may include a muscle sensor sensing movement of a muscle using an electromyographic signal generated when the muscle contracts. The muscle sensor may be attached to a muscle adjacent to the vocal cord.

In addition, the biometric sensor may include a neural sensor sensing a pulse signal of a nerve to predict movement. The biometric sensor may be used with the muscle sensor. For example, the biometric sensor attached to a nerve adjacent to the vocal cord may be connected to the muscle sensor attached to a muscle adjacent to the vocal cord.

The biometric sensor may be recharged by an inductive coupling method. In addition, an implantable neural sensor that hardly requires a power may be used as the biometric sensor.

The mike-sensor may be attached to an upper portion of the vocal cord, and the muscle sensor may be attached to a muscle adjacent to the vocal cord because the muscle sensor senses the electromyographic signal due to contraction of the muscle adjacent to the vocal cord. Moreover, the neural sensor sensing the pulse signal of the nerve adjacent to the vocal cord may be attached to the nerve of the larynx.

The vibration unit 2200 receives the first signal corresponding to the bio-signal and generates a second vibration. The vibration unit 2200 may include a control unit 2210, a driving unit 2220 and a vibration generating unit 2230. The driving unit 2220 may intactly output the first signal as a second signal or may output a second signal different from the first signal by amplifying, attenuating or modulating the first signal. When the second signal is obtained by amplifying, attenuating or modulating the first signal, the second signal may have a different amplitude or a different frequency from the first signal. The vibration generating unit 2230 may generate the second vibration corresponding to the second signal. The control unit 2210 may control the driving unit 2220 and the vibration generating unit 2230 to generate the second vibration.

Operation of the vibration unit 2200 and the sensing unit 2300 will be illustrated. After the sensing unit 2300 senses the bio-signal such as the pulse signal of a nerve, the electromyographic signal, the sound signal and the brain signal corresponding to the first vibration for vocalization, the sensing unit 2300 generates the first signal corresponding to the bio-signal. After the vibration unit 2200 generates the second signal by using the first signal intactly or by amplifying, attenuating or modulating the first signal, the vibration unit 2200 generates the second vibration corresponding to the second signal at a periphery of the vocal cord.

When the vocal cord is removed by ventriculocordectomy, the sensing unit 2300 generates the first signal from the bio-signal corresponding to the first vibration, the driving unit 2220 intactly outputs the first signal as the second signal and the vibration generating unit 2230 generates the second vibration according to the second signal. In addition, when the voice is too loud or too quiet, the sensing unit 2300 generates the first signal from the bio-signal corresponding to the first vibration, the driving unit 2220 outputs the second signal by amplifying, attenuating or modulating the first signal and the vibration generating unit 2230 generates the second vibration according to the second signal. As a result, vocalization can be obtained even when the vocal cord is removed by ventriculocordectomy and vocalization with an appropriate loudness can be obtained even when a voice is too loud or too quiet.

The control unit 2210 controls the driving unit 2220 to intactly output the first signal as the second signal and the vibration generating unit 2230 to generate the second vibration corresponding to the second signal. Alternatively, the control unit 2210 controls the driving unit 2220 to output the second signal by amplifying, attenuating or modulating the first signal and the vibration generating unit 2230 to generate the second vibration corresponding to the second signal.

Accordingly, the control unit 2210 may include a determining unit for setting up an intensity of the second vibration of the vibration unit 2200 so that the control unit 2210 can control the intensity of the second vibration. For example, the control unit 2210 may control the driving unit 2220 such that the second signal outputted from the driving unit 2220 includes information regarding the intensity of the second vibration of the vibration unit 2200.

Figure 2:
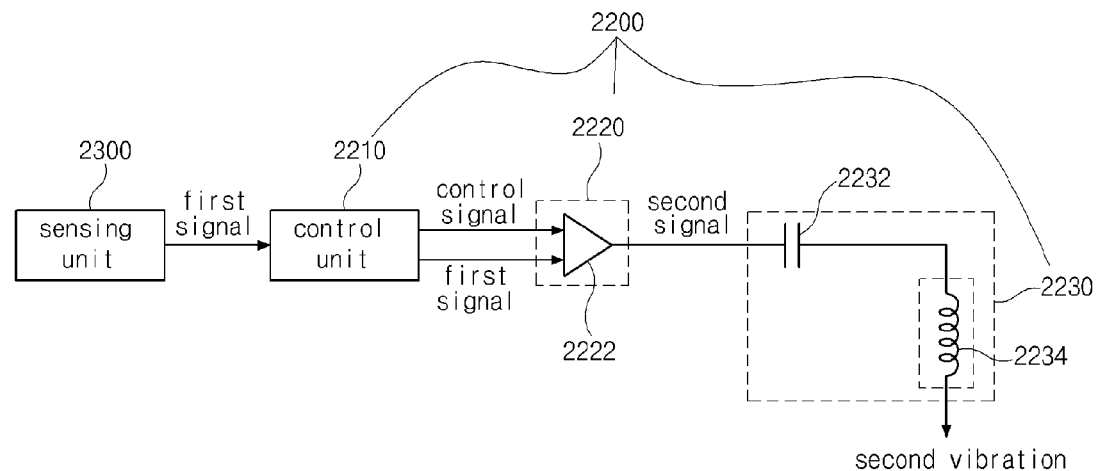
FIG. 2 is a view showing an exemplary electric circuit for a vibration unit of a device for supplementing a voice according to an embodiment of the present invention.

FIG. 2 is a view showing an exemplary electric circuit for a vibration unit of a device for supplementing a voice according to an embodiment of the present invention.

In FIG. 2, a device for supplementing a voice includes a sensing unit 2300 that senses a bio-signal corresponding to a first vibration for vocalization and generates a first signal corresponding to the bio-signal and a vibration unit 2200 that generates a second vibration according to a second signal. The vibration unit 2200 includes a driving unit 2220 that outputs the second signal using the first signal and a vibration generating unit 2230 that generates the second vibration corresponding to the second signal.

The sensing unit 2300 senses the bio-signal such as a pulse signal of a nerve, an electromyographic signal, a sound signal and a brain signal corresponding to the first vibration for vocalization and generates the first signal corresponding to the bio-signal. The sensing unit 2300 may include a current source or a voltage source, and the first signal may include a current or a voltage having a sinusoidal wave.

The driving unit 2220 intactly outputs the first signal as a second signal or outputs a second signal different from the first signal by amplifying, attenuating or modulating the first signal. For example, the driving unit 2220 may include an amplifying unit 2222. The amplifying unit 2222 receives the first signal from the sensing unit 2300 and a control signal from the control unit 2210 and outputs the second signal. For example, the amplifying unit 2222 may include a high voltage operational amplifier (OP-AMP) that is capable of supplying a current sufficient for a magnetic field of the coil 2234 to the vibration generating unit 2230. When the OP-AMP having a gain of 1 is used for the amplifying unit 2222, the driving unit 2220 intactly outputs the first signal as the second signal and the vibration generating unit 2230 generates the second vibration the same as the first vibration. In addition, when the OP-AMP having a gain greater than 1 (e.g., a gain of about 2 to about 10) is used for the amplifying unit 2222, the driving unit 2220 outputs the second signal having an amplitude greater than that of the first signal and the vibration generating unit 2230 generates the second vibration having an amplitude greater than that of the first vibration.

Although the driving unit 2220 includes the amplifying unit 2222 for amplifying a quiet voice in FIG. 8, the driving unit 2220 may further include an attenuating unit for attenuating the first signal in another embodiment. For example, the driving unit 2220 including an attenuating unit having a gain smaller than 1 (e.g., a gain of about ½ to about 1/10) may output the second signal having an amplitude smaller than that of the first signal and the vibration generating unit 2230 may generate the second vibration having an amplitude smaller than that of the first vibration. In addition, the driving unit 2220 may further include a frequency modulating unit for modulating a frequency of the first signal in another embodiment. For example, the driving unit 2220 including a frequency modulating unit may output the second signal having a frequency different from that of the first signal and the vibration generating unit 2230 may generate the second vibration having a frequency different from that of the first vibration.

Since the driving unit 2220 including the amplifying unit, the attenuating unit and the frequency modulating unit outputs the second signal having the same amplitude, the amplified amplitude, the attenuated amplitude or the modulated frequency as compared with the first signal, the device 2000 including the driving unit 2220 may supplement a voice to have the same loudness, the amplified loudness, the attenuated loudness or the different pitch.

The vibration generating unit 2230 may include a capacitor 2232 and a coil 2234. The capacitor 2232 for matching an impedance of the coil 2234 may be connected to the coil 2234 in series, and the coil 2234 may generate the second vibration using an electromagnetic induction. The coil 2234 may be referred to as a voice coil or an inductor.

Figure 3:
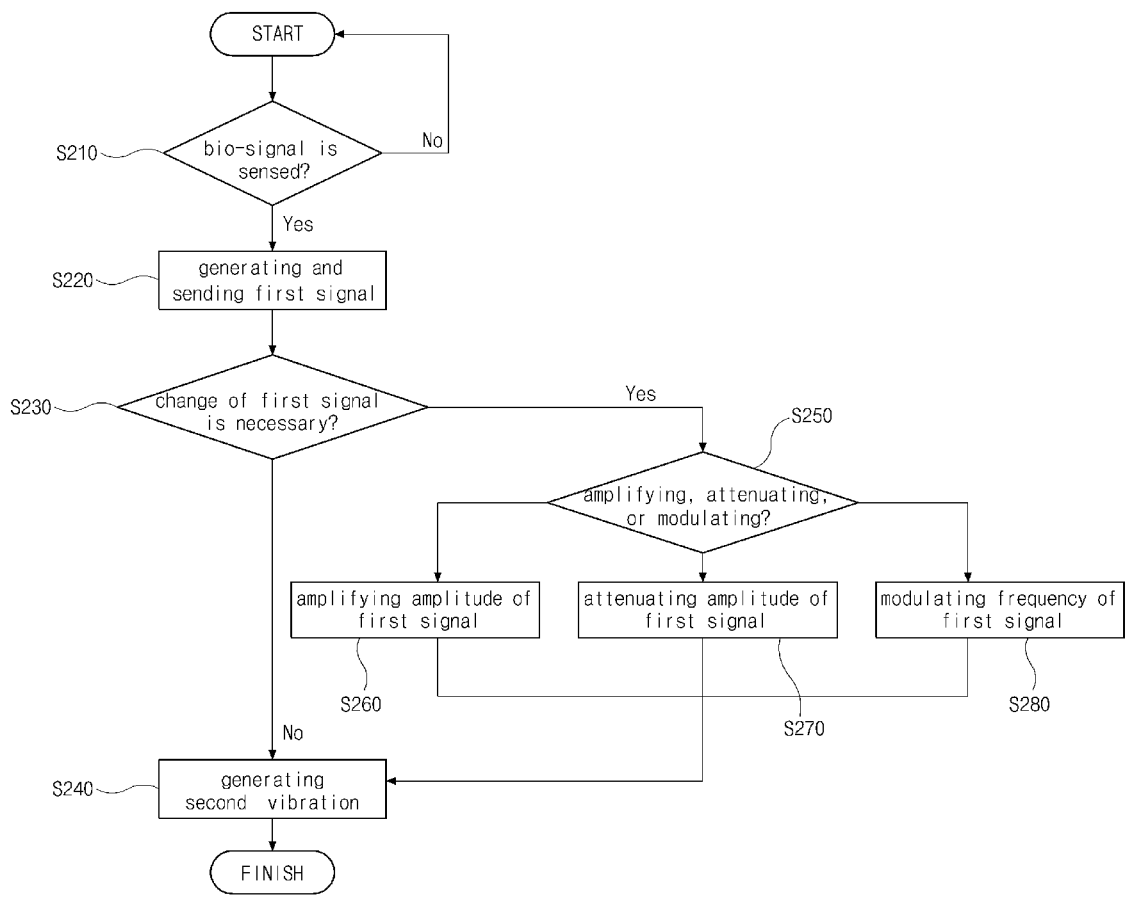
FIG. 3 is a flow chart illustrating a method of controlling a device for supplementing a voice according to an embodiment of the present invention.

FIG. 3 is a flow chart illustrating a method of controlling a device for supplementing a voice according to an embodiment of the present invention.

At step S210, the sensing unit 2300 judges whether the bio-signal corresponding to the first vibration for vocalization is sensed or not. When the bio-signal is not sensed, the process returns to the start step. When the bio-signal is sensed, the sensing unit 2300 generates the first signal corresponding to the bio-signal and sends the first signal to the vibration unit 2200 at step S220.

At step S230, the control unit 2210 of the vibration unit 2200 judges whether change of the first signal is necessary or not. When the first signal relates to the proper voice, it is not necessary to change the first signal and the driving unit 2220 intactly sends the first signal as the second signal to the vibration generating unit 2230. In addition, the vibration generating unit 2230 generates the second vibration according to the second signal that is the same as the first signal at step S240. When the first signal relates to the voice that is too loud, too quiet or too hoarse, it is necessary to change the first signal and the driving unit 2220 changes the first signal to the second signal at steps S250, S260, S270 and S280. For example, the driving unit 2220 may generate the second signal by amplifying the amplitude of the first signal at step S260, by attenuating the amplitude of the first signal at step S270 or modulating the frequency of the first signal at step S280. In addition, the vibration generating unit 2230 generates the second vibration according to the second signal that has the amplified amplitude, the attenuated amplitude or the modulated frequency as compared with the first signal.

FIGS. 4A to 4G are views showing installation states of a device for supplementing a voice according to an embodiment of the present invention. Although a normal vocal cord is shown in FIGS. 4A to 4G, the device for supplementing a voice may be applied to a partially disabled vocal cord or a wholly disabled vocal cord. Further, although a vocal cord of human beings is shown in FIGS. 4A to 4G, the device for supplementing a voice may be applied to animals.

Figure 4A:
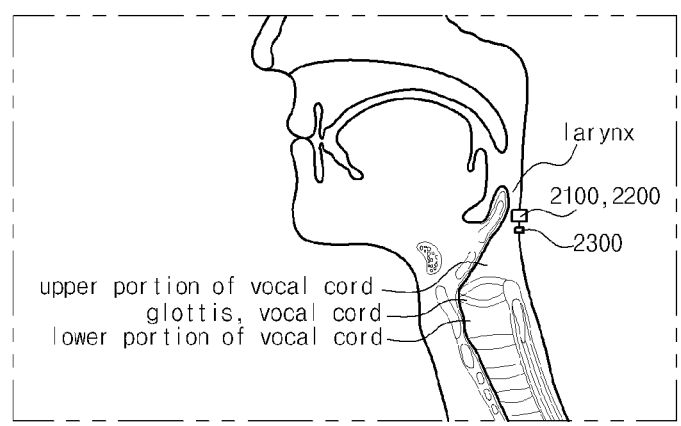
FIGS. 4A to 4G are views showing installation states of a device for supplementing a voice according to an embodiment of the present invention.
Figure 4B:
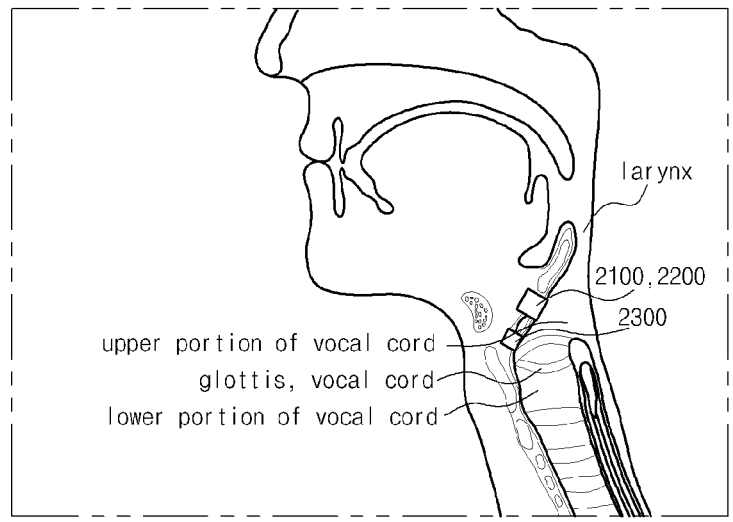
Figure 4C:
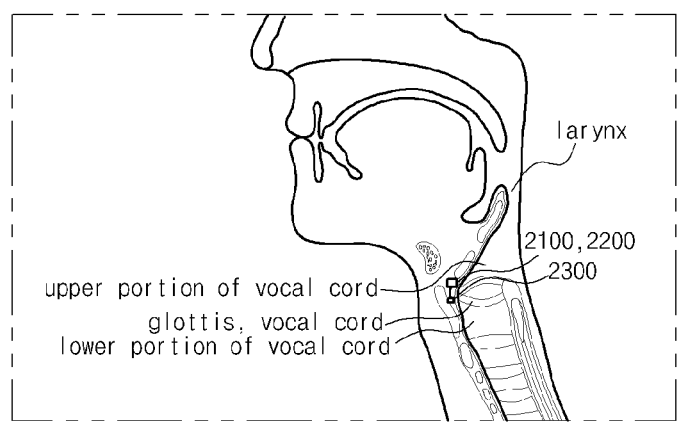
Figure 4D:
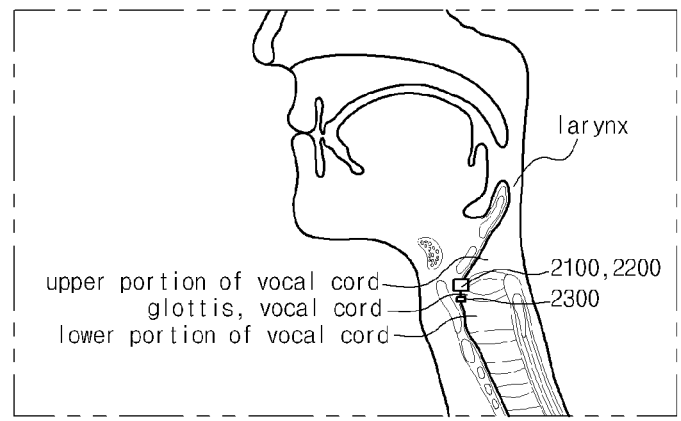
Figure 4E:
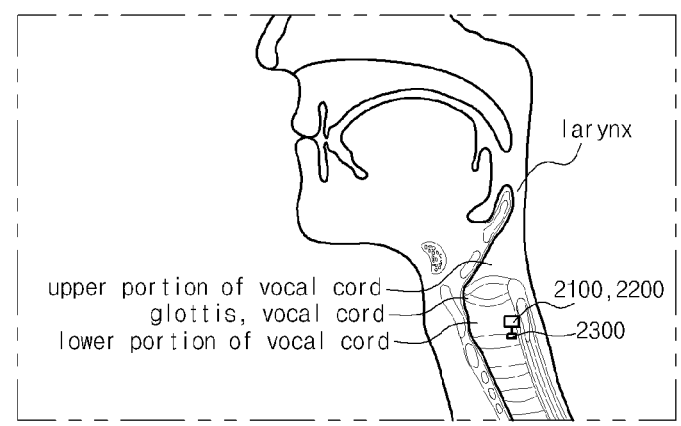

The device 2000 including the power unit 2100, the vibration unit 2200 and the sensing unit 2300 may be installed at an upper portion of the larynx as shown in FIG. 4A, and the device 2000 including the power unit 2100, the vibration unit 2200 and the sensing unit 2300 may be installed at an upper portion of the vocal cord as shown in FIG. 4B. In addition, the device 2000 including the power unit 2100, the vibration unit 2200 and the sensing unit 2300 may be installed at an outer portion of the subcutaneous tissue adjacent to the vocal cord as shown in FIG. 4C, the device 2000 including the power unit 2100, the vibration unit 2200 and the sensing unit 2300 may be installed at the subcutaneous tissue adjacent to the vocal cord as shown in FIG. 4D, and the device 2000 including the power unit 2100, the vibration unit 2200 and the sensing unit 2300 may be installed at a lower portion of the vocal cord (i.e. subglottis area) as shown in FIG. 4E. Further, the power unit 2100 may be installed at an outer portion of the vocal cord and the vibration unit 2200 and the sensing unit 2300 may be installed at a lower inner portion of the vocal cord as shown in FIG. 4E Moreover, the device 2000 including the power unit 2100, the vibration unit 2200 and the sensing unit 2300 may be surrounded by a capsule and may be installed at a portion adjacent to the vocal cord as shown in FIG. 4G.

The device 2000 may be installed at a cervical portion or a portion adjacent to the vocal cord. For example, the device 2000 may have a hanging type where the device 2000 is hung on a cervical portion. In addition, the device 2000 may have an attaching type where the device 2000 is attached to the vocal cord or the tissue adjacent to the vocal cord using a biocompatible medical adhesive such as a cyanoacrylate adhesive of liquefied monomer (methyl/ethyl/n-butyl group), a fibrin glue using tissue conglutination, a gelatin glue (e.g., cross-linked gelatin-resorcinol-formaldehyde (GRF)) and polyurethane adhesive. Further, as an implanting type, after the vocal cord or the subcutaneous tissue adjacent to the vocal cord is cut out, the device 2000 may be implanted and may be covered with the subcutaneous tissue. When the device 2000 is implanted in the vocal cord, the device 2000 may be implanted without damage such that the device 2000 is surrounded by a biocompatible material.

Each of the power unit 2100, the vibration unit 2200 and the sensing unit 2300 of the device 2000 may be independently installed at one of the upper portion of the larynx, the upper portion of the vocal cord, the outer portion of the subcutaneous tissue adjacent to the vocal cord, the subcutaneous tissue adjacent to the vocal cord, the lower portion of the vocal cord and the portion adjacent to the vocal cord, and the power unit 2100, the vibration unit 2200 and the sensing unit 2300 may be connected to one another through a conductive connection line.

Figure 4F:
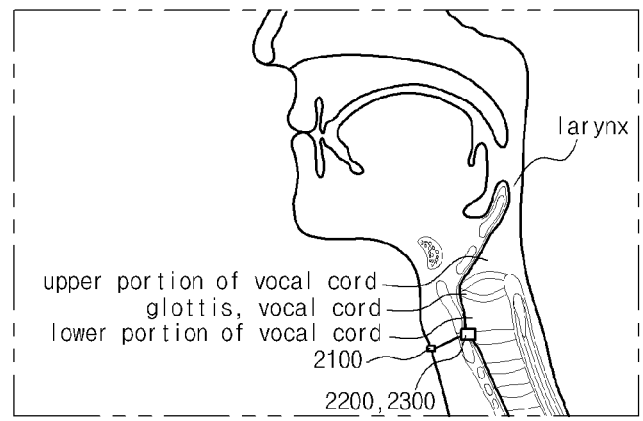
Figure 4G:
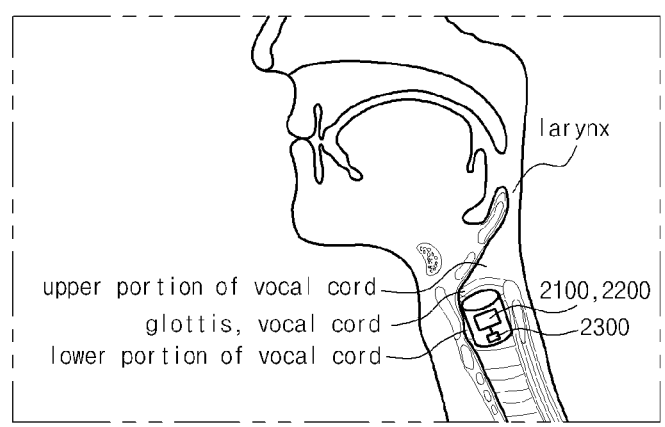

The power unit 2100 may be installed at the outer portion of a body as shown in FIG. 4F and may be installed at the inner portion of a body as shown in FIGS. 4A to 4E and 4G. The power unit 2100 may be recharged by an electromagnetic induction method. Similarly to a wireless recharger, for example, a recharging pad may be disposed adjacent to the power unit 2100 and the magnetic field generated by the first coil of the recharging pad may induce the current in the second coil of the power unit 2100. In addition, the power unit 2100 at the outer portion or the inner portion of the cervical portion may be recharged by the current of the second coil.

Further, the power unit 2100 may include a transplatable battery such as a nano battery, a biofuel cell that attains electricity during an oxidation process of glucose using enzyme and a biocompatible fuel cell that uses a biopolymer film of nucleic acid/amino acid/protein.

Moreover, the power unit 2100 may be recharged by a human body communication (HBC) method using the body as a medium for communication. For example, when a voltage is applied to an external electrode, a surface electric field of a body separated from the external electrode by an insulator may be changed and the power unit 2100 may be recharged.

The sensing unit 2300 senses the bio-signal corresponding to the first vibration for vocalization. A muscle such as a vocal ligament, a vocalis and a arytenoideus (e.g. a lateral circoarytenoideus, a lateral thryoarytenoideus, a trasverse arytenoideus, an oblique arytenoideus, a posterior circoarytenoideus) may contract for vocalization. Since a portion of the muscle for vocalization remains even when the ventriculocordectomy is performed, the sensing unit 1300 may sense the electromyographic signal according to contraction of the muscle as a bio-signal.

In addition, a nerve such as a superior laryngeal nerve, an internal branch, an external branch, an ansa galeni and arecurrent layngeal nerve may relate to vocalization through contraction of an interior constrictor muscle. Since a portion of the nerve for vocalization remains even when the ventriculocordectomy is performed, the sensing unit 2300 may sense the pulse signal of the nerve as a bio-signal.

As a result, the sensing unit 2300 may be installed adjacent to a portion corresponding to the bio-signal. For example, a muscle sensor as the sensing unit 2300 may be installed on the muscle at the periphery of the vocal cord, and a nerve sensor as the sensing unit 2300 may be installed at the laryngeal nerve. Further, a mike-sensor as the sensing unit 2300 may be installed at the periphery of the vocal cord.

The device 2000 of FIGS. 4A to 4G has a mouth type where the power unit 2100, the vibration unit 2200 and the sensing unit 2300 are inserted through the mouth as a tube shape and the vibration is generated in the mouth. In another embodiment, the device may have a neck type where the vibration unit 2200 contacts the neck and artificially vibrates the sphincter.

In a device for supplementing a voice according to the present disclosure, since a second vibration that corresponds to or modified from a first vibration of an original voice is directly provided adjacent to a vocal cord from a bio-signal such as a pulse signal of a nerve, an electromyographic signal, a sound signal and a brain signal, an excellent vocalization can be obtained. In addition, since a first vibration of an original voice that is too loud, too quiet or too hoarse is reduced using a third vibration, a quality of vocalization is improved.

It will be apparent to those skilled in the art that various modifications and variations can be made in the present disclosure without departing from the spirit or scope of the invention. Thus, it is intended that the present invention cover the modifications and variations of this invention provided they come within the scope of the appended claims and their equivalents.

What is claimed is:

1. A device for supplementing a voice, comprising:
a sensing unit configured to sense a signal corresponding to a first vibration of vocalization and generate a first signal corresponding to the sensed signal;
a vibration unit configured to generate a second vibration using the first signal; and
a power unit configured to supply a power to the sensing unit and the vibration unit, wherein
the vibration unit comprises:
a control unit configured to
generate a first control signal according to the first signal, and
determine whether change of the first signal is necessary; and
a vibration driving unit configured to
generate a second signal by sending the first signal as the second signal to a vibration generating unit in response to the control unit determining that change of the first signal is not necessary, and
generate the second signal by amplifying the amplitude of, attenuating the amplitude of, or modulating the frequency of the first signal in response to the control unit determining that change of the first signal is necessary; and
the vibration generating unit configured to
be installed adjacent to a vocal cord or larynx inside a human body and to generate the second vibration based on the second signal.

2. The device according to claim 1, wherein the sensed signal includes one of a pulse signal of a nerve, an electromyographic signal, a sound signal and a brain signal relating to the vocalization.

3. The device according to claim 1, wherein the vibration unit comprises:
the vibration generating unit configured to generate the second vibration according to the second signal.

4. The device according to claim 3, wherein the second signal has one of a same amplitude and a same frequency, an amplified amplitude, an attenuated amplitude and a modulated frequency as compared with the first signal.

5. The device according to claim 3, wherein the vibration generating unit is configured to generate the second vibration using an electromagnetic induction between a magnet and a coil.

6. The device according to claim 3, wherein the vibration generating unit is configured to generate the second vibration using a piezoelectric phenomenon.

7. A method of controlling a device for supplementing a voice, comprising:
sensing a signal corresponding to a first vibration of vocalization;
generating a first signal corresponding to the sensed signal; and
generating a second vibration using the first signal, wherein the generating of the second vibration comprises
determining whether change of the first signal is necessary;
generating a second signal by amplifying the amplitude of, attenuating the amplitude of, or modulating the frequency of the first signal in response to the determining that change of the first signal is necessary; and
generating the second vibration using a vibration generating unit disposed adjacent to a vocal cord or larynx inside a human body based on the second signal.

8. The method according to claim 7, wherein the sensed signal includes one of a pulse signal of a nerve, an electromyographic signal, a sound signal and a brain signal relating to the vocalization.

9. The method according to claim 7, wherein the generating of the second vibration using the first signal comprises:
generating a first control signal according to the first signal;
sending the first signal to the vibration generating unit in response to the determining that change of the first signal is not necessary,
wherein the vibration generating unit generates the second vibration using the second signal and the first control signal.

10. The method according to claim 9, wherein generating the second signal comprises:
analyzing the first signal; and
generating the second signal by one of intactly outputting the first signal, amplifying an amplitude of the first signal, attenuating an amplitude of the first signal and modifying a frequency of the first signal.

11. The device according to claim 3, wherein the control unit comprises a determining unit that measures an intensity of the second vibration and controls the intensity of the second vibration.

12. The device according to claim 1, wherein the vibration driving unit comprises an OP-AMP configured to receive the first signal from the sensing unit and the first control signal from the control unit, and configured to output the first signal as the second signal in response to a gain of the OP-AMP having a value of 1, and to output the second signal having an amplitude greater than that of the first signal in response to the gain of the OP-AMP having a value greater than 1.

13. The device according to claim 1, wherein the power unit comprises at least one of a biofuel cell that attains electricity during an oxidation process of glucose using enzyme and a biocompatible fuel cell using a biopolymer film of nucleic acid/amino acid/protein.

14. The device according to claim 1, wherein the power unit is configured to be recharged in response to a surface electric field of a human body being changed, and in response to a voltage being applied to an external electrode.

15. A device for supplementing a voice, comprising:
a sensing unit configured to sense a signal corresponding to a first vibration of vocalization and to generate a first signal corresponding to the sensed signal;
a vibration unit configured to generate a second vibration using the first signal; and
a power unit configured to supply a power to the sensing unit and the vibration unit, wherein
the vibration unit comprises:
a control unit configured to
generate a first control signal according to the first signal, and
determine whether change of the first signal is necessary; and
a vibration driving unit configured to
generate a second signal by sending the first signal to a vibration generating unit as the second signal in response to the control unit determining that change of the first signal is not necessary, and generate the second signal by amplifying, attenuating or modulating the first signal in response to the control unit determining that change of the first signal is necessary; and the vibration generating unit configured to generate the second vibration based on the second signal, wherein the vibration unit is configured to reduce the first vibration using a third vibration.

16. The device according to claim 1, wherein the sensing unit comprises a biometric sensor configured to sense a pulse signal of a nerve to predict movement and a muscle sensor connected to the biometric sensor and configured to sense movement of a muscle using an electromyographic signal generated in response to a contraction of the muscle.

17. A device for supplementing vocalization vibration, comprising:

a sensing unit configured to sense a signal corresponding to a first vocalization vibration and generate a first signal corresponding to the sensed signal; and a vibration unit configured to be installed at or adjacent to a vocal cord or larynx inside a human body, and configured to determine whether a change to the first vocalization vibration is necessary to enhance speech generation, and, in response to a determination that the change is necessary, generate a second vocalization vibration different from the first vocalization vibration by amplifying, attenuating or modulating the first signal.

18. The device according to claim 17, wherein the vibration unit is configured to generate a third vocalization vibration to reduce the first vocalization vibration.

19. The device according to claim 17, wherein the sensed signal comprises at least one of a pulse signal of a nerve, an electromyographic signal, a sound signal and a brain signal relating to the vocalization.

20. A device for generating or supplementing vocalization vibration in a user with a vocal cord disability, the device comprising:

a sensing unit configured to generate a first signal based on at least one of a vocal cord vibration for vocalization, a pulse signal of a nerve for vocalization, an electromyographic signal for vocalization, a sound signal for vocalization and a brain signal for vocalization; and a vibration unit configured to be installed at or adjacent to a vocal cord or larynx inside a human body, and configured to generate a vocalization vibration as sound energy within a vocal track of a user based on the first signal.

21. The device according to claim 20, wherein the vibration unit comprises a voice coil configured to generate the vocalization vibration.

22. The device according to claim 20, wherein the vibration unit is configured to generate the vocalization vibration in the user whose vocal cord is removed.

23. The device according to claim 20, wherein the vibration unit is configured to generate the vocalization vibration by using a piezoelectric phenomenon or an electromagnetic induction between a magnet and a voice coil.

* * * * *